(12) United States Patent
Lee

(10) Patent No.: US 10,695,300 B2
(45) Date of Patent: Jun. 30, 2020

(54) PATCH-TYPE WOUND DRESSING COMPRISING METHYLENE BLUE MIXTURE FOR TREATING SKIN WOUND

(71) Applicant: D. R. NANO CO., LTD., Seoul (KR)

(72) Inventor: Yong Deok Lee, Seoul (KR)

(73) Assignee: D.R. NANO Co., Ltd., Seoul (KR)

( * ) Notice: Subject to any disclaimer, the term of this patent is extended or adjusted under 35 U.S.C. 154(b) by 0 days.

(21) Appl. No.: 16/167,563

(22) Filed: Oct. 23, 2018

(65) Prior Publication Data

US 2019/0224134 A1 Jul. 25, 2019

(51) Int. Cl.
| | |
|---|---|
| *A61K 9/70* | (2006.01) |
| *A61L 15/20* | (2006.01) |
| *A61L 15/60* | (2006.01) |
| *A61L 15/46* | (2006.01) |
| *A61K 31/5415* | (2006.01) |
| *A61K 41/00* | (2020.01) |
| *A61K 47/12* | (2006.01) |
| *A61K 47/14* | (2017.01) |
| *A61K 47/18* | (2017.01) |
| *A61K 47/22* | (2006.01) |
| *A61K 47/28* | (2006.01) |

(52) U.S. Cl.
CPC ........ *A61K 9/7084* (2013.01); *A61K 31/5415* (2013.01); *A61K 41/0057* (2013.01); *A61K 47/12* (2013.01); *A61K 47/14* (2013.01); *A61K 47/183* (2013.01); *A61K 47/22* (2013.01); *A61K 47/28* (2013.01); *A61L 15/20* (2013.01); *A61L 15/46* (2013.01); *A61L 15/60* (2013.01); *A61L 2300/404* (2013.01); *A61L 2300/442* (2013.01); *A61L 2300/802* (2013.01)

(58) Field of Classification Search
CPC . A61L 15/46; A61L 2300/442; A61K 9/7084; A61K 31/202; A61F 13/00063; A61F 2013/00727; A61F 2013/00906; A61F 2013/0091; A61P 17/02
See application file for complete search history.

(56) References Cited

U.S. PATENT DOCUMENTS

| | | | | |
|---|---|---|---|---|
| 8,389,583 B2 * | 3/2013 | Ash | .............. | A01N 31/02 514/724 |
| 8,563,799 B2 | 10/2013 | Kamakura et al. | | |
| 2016/0310440 A1 * | 10/2016 | Lai | .............. | A61K 31/65 |

FOREIGN PATENT DOCUMENTS

| | | | | |
|---|---|---|---|---|
| CA | 2496439 A1 * | 4/2004 | ......... | A61F 13/0203 |
| KR | 10-15114058 B1 | 4/2015 | | |
| KR | 10-1667404 B1 | 10/2016 | | |

OTHER PUBLICATIONS

Marilyn T Wan, Jennifer Y Lin, "Current evidence and applications of photodynamic therapy in dermatology" Clinical, Cosmetic and Investigational Dermatology, 7 (1): 145-163.

* cited by examiner

*Primary Examiner* — Andrew S Rosenthal

(57) ABSTRACT

There is provided a wound dressing prepared with a hydrocolloid gel, a polyurethane film, a PVA hydrogel, an alginate gel or the like, which has excellent stretchability and exudation absorbency of the wound surface for protection and prevention of infection on the wound surface in which continuity of a body tissue is destroyed by a physical impact or the like, can maintain a wet environment suitable for promoting healing of the wound surface, and has no pain or no worry to damage regenerated skin when the wound dressing is exchanged.

6 Claims, 5 Drawing Sheets

PATCH-TYPE WOUND DRESSING COMPRISING METHYLENE BLUE MIXTURE FOR TREATING SKIN WOUND

CROSS REFERENCE TO RELATED APPLICATION

This application claims priority from and the benefit of Korean Patent Application No. 10-2018-0007575, filed on Jan. 20, 2018, which is hereby incorporated by reference for all purposes as if fully set forth herein.

BACKGROUND

Field

The present disclosure relates to a patch-type wound dressing for protecting the wound of skin, in which the wound dressing comprises a transdermal material which is made of a material such as a hydrocolloid gel which is biocompatible with a living body and its skin to be attached to, and a mixture containing methylene blue and an organic acid as a composition having an antibacterial characteristic included in the transdermal material.

The present disclosure relates to a wound dressing prepared by a hydrocolloid gel, a polyurethane film, a PVA hydrogel, an alginate gel or the like, which has excellent stretchability and exudation absorbency of the wound surface for protecting the wound surface in which continuity of a body tissue is destroyed by a physical impact or the like, can maintain a wet environment suitable for promoting prevention of infection and healing of the wound surface, and has no pain or no worry to damage regenerated skin when the wound dressing is replaced.

Further, the present disclosure relates to a composition for promoting healing through the prevention of infection on the attached surface of the wound dressing or on the wound surface. The wound dressing has a sterilization effect on *Staphylococcus aureus* and the like and an effect on psoriasis and acne and uses a mixture of a methylene blue component used as a photosensitizer in photodynamic therapy for various skin diseases and an organic acid mixed with the methylene blue to impart hydrophobicity as an active ingredient.

Discussion of the Background

The basic concept of photodynamic therapy (PDT) uses the principle that a photosensitizer exposed to light generates singlet oxygen and other reactive oxygen species to kill the bacteria that cause inflammation and is introduced as a method which can reduce *Staphylococcus aureus* and the like by an sterilization effect of active oxygen, vascular occlusion, immunity, and apoptosis against *Staphylococcus aureus* which may induce purulent inflammation and prevent the spread of abnormally enlarged skin wound. Currently, operations using the PDT have been performed in many hospitals and clinics.

This therapy is a method in which when a photosensitizer is first applied on the skin surface, the photosensitizer is selectively absorbed in the skin, when light of a specific wavelength is irradiated thereto, the photosensitizer in the sebaceous gland and the pores is activated and singlet oxygen is generated so that the sebaceous gland is destroyed, the fungi and the like in the pores are killed, and a keratolysis (peeling) effect of the skin surface is caused, and as a result, the sebum discharge is facilitated through the peeling effect of removing the dead skin blocking the pores.

In a patch-type formulation for protecting and healing skin wound and preventing infection of the related art, active ingredients of ointment, cream, or the like are used instead of a photosensitive component and thus its skin regeneration speed is rather slow. However, in various embodiments of the present invention, the mixture of methylene blue and an organic acid having a photosensitive therapy effect is used as an active ingredient so that the regeneration of damaged skin is more efficient than the related art.

In addition, the patch-type formulation made of the hydrocolloid gel or the like used in the present invention is excellent in absorbency, maintenance of wetness, prevention of intrusion of bacteria, prevention of bacterial growth, mechanical strength and adhesiveness which are requirements as a wound dressing material. Currently, patch-type formulations are variously applied to obtain efficacy such as wound healing, sterilization, scar tissue prevention, scar tissue inhibition, and wound restoration against burns, trauma, wound, pressure sores, and skin diseases.

Methylene blue has been studied as various therapeutic materials due to antimicrobial and photodynamic effects (Marilyn T Wan, Jennifer Y Lin. Current evidence and applications of photodynamic therapy in dermatology. Clinical, Cosmetic and Investigational Dermatology 7 (1): 145-163), and recently, studies and skin disease PDT using the antimicrobial effect of the methylene blue have been used. However, since methylene blue is difficult to pass through a membrane of a cell or a lipid layer of a skin as a hydrophilic molecule and has low target directivity, in order to use methylene blue as a photosensitizer effective for damaged skin and for target-oriented therapy, it is necessary to convert the properties of methylene blue by combining the methylene blue with other organic acids.

SUMMARY OF THE INVENTION

An object of the present invention is to provide a patch-type wound dressing prepared in a hydrocolloid gel or the like for protection, prevention of infection and healing of the wound of the skin and the like, in which methylene blue that has an antimicrobial effect and is widely used as a photosensitizer for photodynamic therapy is used as an active ingredient for prevention of infection and healing of the skin wound in the wound dressing.

Since the methylene blue is hydrophilic and difficult to pass through a membrane of a cell or a lipid layer of skin and has low target directivity, in order to use methylene blue as a photosensitizer effective for damaged skin and for target-oriented therapy, it is necessary to convert the properties of methylene blue by combining the methylene blue with other organic acids.

In accordance with one aspect of the present invention, there are provided examples of organic acids used for changing the properties of methylene blue, which may include docosahexaenoic acid (DHA), indole-3-acetic acid (IAA), tranexamic acid, salicylic acid, ascorbic acid, linoleic acid, linolenic acid, oleic acid, deoxycholic acid, folic acid, retinoic acid, acid, cholic acid, glycocholic acid, taurocholic acid, chenodeoxycholic acid, glycochenodeoxycholic acid, taurochenodeoxycholic acid, lithocholic acid, salicylsalicylic acid, acetylsalicylic acid, methyl salicylic acid, and phenylacetic acid. When the methylene blue and the organic acid component are combined, the methylene blue and the organic acid component are physically bound to each other to form a mixture.

Other aspects, advantages, and salient features of the invention will become apparent to those skilled in the art from the following detailed description, which, taken in conjunction with the annexed drawings, discloses exemplary embodiments of the invention.

BRIEF DESCRIPTION OF THE DRAWINGS

The above and other aspects, features and advantages of certain exemplary embodiments of the present invention will be more apparent from the following description taken in conjunction with the accompanying drawings.

DETAILED DESCRIPTION OF EXEMPLARY EMBODIMENTS

The following description with reference to the accompanying drawings is provided to assist in a comprehensive understanding of exemplary embodiments of the invention as defined by the claims and their equivalents. It includes various specific details to assist in that understanding but these are to be regarded as merely exemplary. Accordingly, those of ordinary skilled in the art will recognize that various changes and modifications of the embodiments described herein can be made without departing from the scope and spirit of the invention. In addition, descriptions of well-known functions and constructions may be omitted for clarity and conciseness.

The terms and words used in the following description and claims are not limited to the bibliographical meanings, but, are merely used by the inventor to enable a clear and consistent understanding of the invention. Accordingly, it should be apparent to those skilled in the art that the following description of exemplary embodiments of the present invention is provided for illustration purpose only and not for the purpose of limiting the invention as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It will be understood that when an element or layer is referred to as being "on" or "connected to" another element or layer, it can be directly on or directly connected to the other element or layer, or intervening elements or layers may be present. In contrast, when an element is referred to as being "directly on" or "directly connected to" another element or layer, there are no intervening elements or layers present. It will be understood that for the purposes of this disclosure, "at least one of X, Y, and Z" can be construed as X only, Y only, Z only, or any combination of two or more items X, Y, and Z (e.g., XYZ, XYY, YZ, ZZ).

Figure 1:
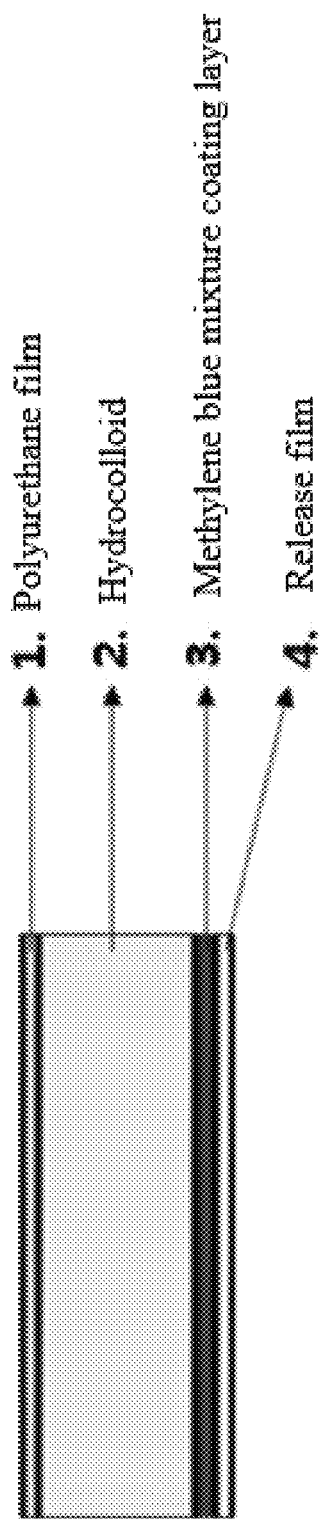
FIG. 1 is a schematic diagram for describing a wound dressing containing a methylene blue mixture in accordance with one exemplary embodiment of the present invention.

Referring to FIG. 1, a wound dressing containing a methylene blue mixture in accordance with one exemplary embodiment of the present invention is illustrated. For instance, a wound dressing according to one exemplary embodiment may include a polyurethane film 1 as a base layer, hydrocolloid 2, a methylene blue-coated layer 3, and a detachable cover layer 4. In accordance with exemplary embodiments of the present invention, a wound dressing for promoting healing of damaged skin may be a patch type made of a hydrocolloid gel or the like and include a methylene blue mixture containing methylene blue and one or more kinds of organic acids as an active ingredient.

The material for preparing the patch-type dressing used in the present invention is excellent in absorbency, maintenance of wetness, prevention of intrusion of bacteria, prevention of bacterial growth, mechanical strength and adhesiveness which are requirements as a wound dressing material, and thus all materials having efficacy such as wound healing, sterilization, scar tissue prevention, scar tissue inhibition, and wound restoration against burns, trauma, wound, pressure sores, and skin diseases may be applied.

For example, the hydrocolloid gel is excellent in absorbency because hydrophilic colloid particles contained in a hydrophobic substrate absorb exudates by swelling, a PVA hydrogel is excellent in maintenance of wet environment, pain relief by cooling effect because the PVA hydrogel contains about 80% of purified water in the preparation, and transparency, and an alginate gel is excellent in hemostatic and exudate absorbency.

In terms of the mass ratio of methylene blue, organic acid 1 and organic acid 2 for forming the methylene blue mixture of the present invention, the mass of the organic acid 1 is 1 to 5 times greater than the mass of methylene blue, and the mass of the organic acid 2 is 50 to 500 times greater than the mass of the mixture of the methylene blue and the organic acid 1 in accordance with one exemplary embodiment. The organic acids 1 and 2 may be different organic acids.

A wound dressing in accordance with one exemplary embodiment of the present invention may be formed by laminating a hydrocolloid gel as a transdermal material to be in contact with the skin on a polyurethane film substrate, applying the methylene blue mixture to the hydrocolloid gel transdermal material, and finally attaching a release film. The hydrocolloid gel may be replaced with a polyurethane film, a PVA hydrogel, an alginate gel, or the like.

The wound dressing applied with the methylene blue mixture may be prepared by preparing a quadrangular patch type transdermal material using a hydrocolloid gel and applying uniformly the active ingredient mixed with methylene blue and two kinds of organic acids to the transdermal material in an amount of 0.1 to 100 μg, preferably 10 to 50 μg per a unit area of 1 cm of a width and 1 cm of a length.

When the amount of the methylene blue mixture is less than 0.1 μg, the amount of the methylene blue mixture is too small and the effect of preventing wound infection is small, and when the amount exceeds 100 μg, the consumption of the methylene blue mixture may be too high.

Figure 2:
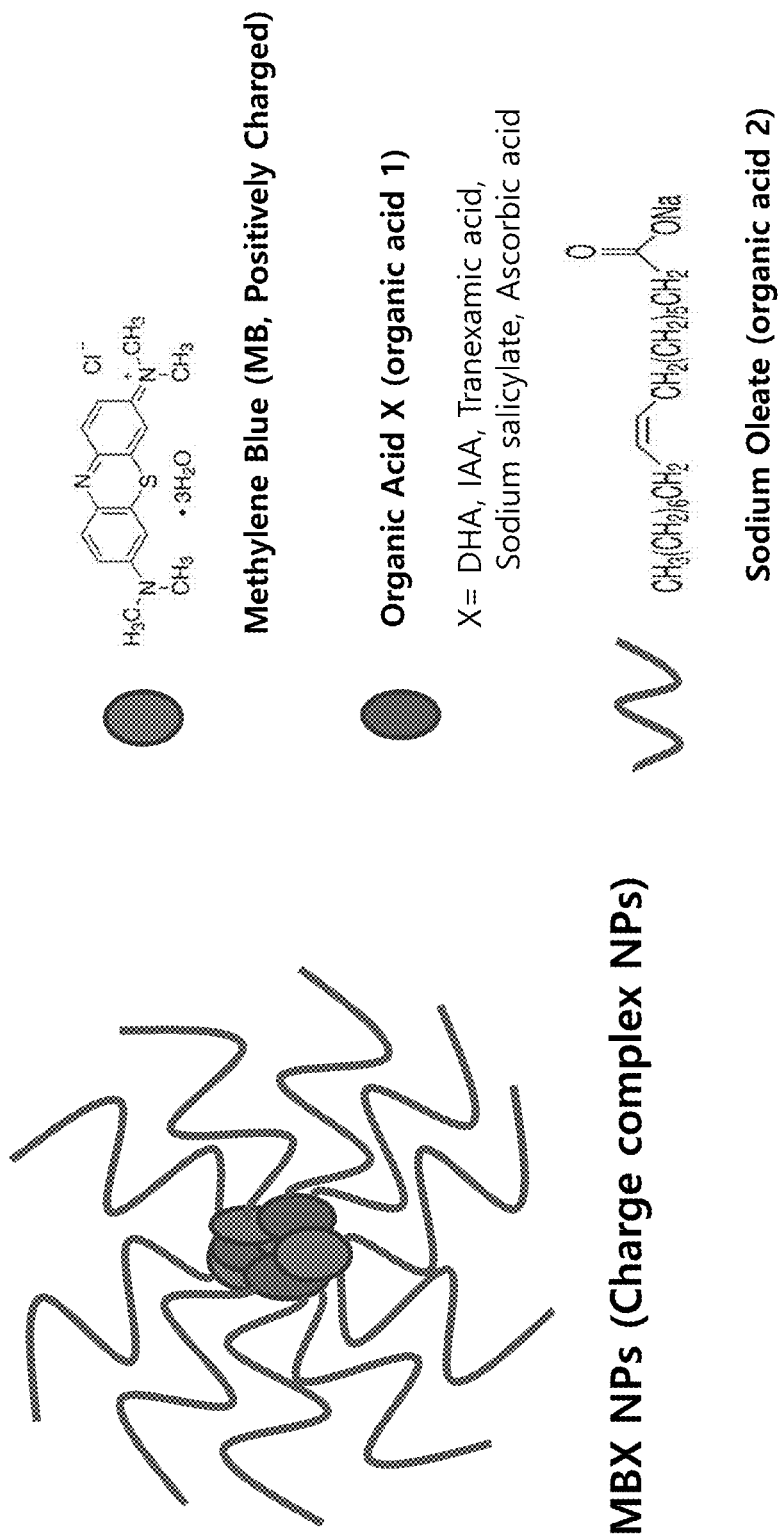
FIG. 2 is a schematic diagram of a mixture of methylene blue and two kinds of organic acids as active ingredients for the prevention of infection or promotion of wound healing, which protect skin wounds and kill surrounding harmful bacteria in accordance with one exemplary embodiment of the present invention.

In accordance with one exemplary embodiment of the present invention, a surfactant used in the methylene blue mixture may use oleic acid. Referring to FIG. 2, a mixture of methylene blue and two kinds of organic acids as active ingredients for prevention of infection or promotion of wound healing is schematically illustrated. These active ingredients in accordance with one exemplary embodiment are believed to protect skin wounds and kill surrounding harmful bacteria when applied to damaged skin.

Examples of the organic acids used in the methylene blue mixture may include docosahexaenoic acid (DHA), indole-3-acetic acid (IAA), tranexamic acid, salicylic acid, ascorbic acid, linoleic acid, linolenic acid, oleic acid, deoxycholic acid, folic acid, retinoic acid, acid, cholic acid, glycocholic acid, taurocholic acid, chenodeoxycholic acid, glycochenodeoxycholic acid, taurochenodeoxycholic acid, lithocholic acid, salicylsalicylic acid, acetylsalicylic acid, methyl salicylic acid, and phenylacetic acid are compounds represented by the following Chemical Formulas 1 to 22 below and most preferably, a methylene blue mixture using salicylic acid and oleic acid.

Chemical Formula 1

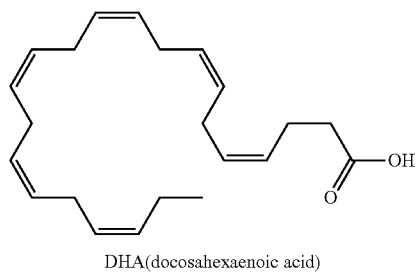

DHA (docosahexaenoic acid)

Chemical Formula 2

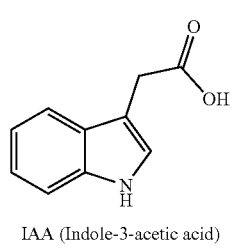

IAA (Indole-3-acetic acid)

Chemical Formula 3

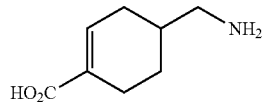

Tranexamic acid

Chemical Formula 4

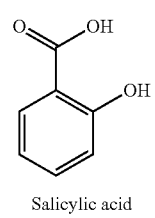

Salicylic acid

Chemical Formula 5

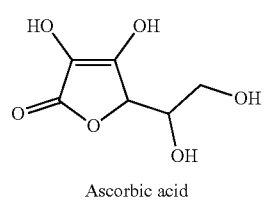

Ascorbic acid

Chemical Formula 6

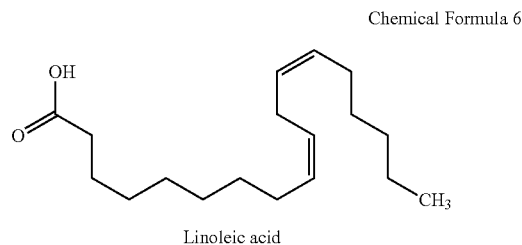

Linoleic acid

Chemical Formula 7

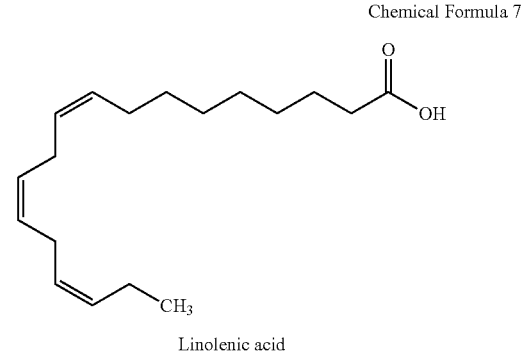

Linolenic acid

Chemical Formula 8

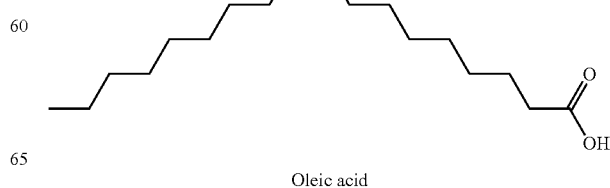

Oleic acid

Chemical Formula 9
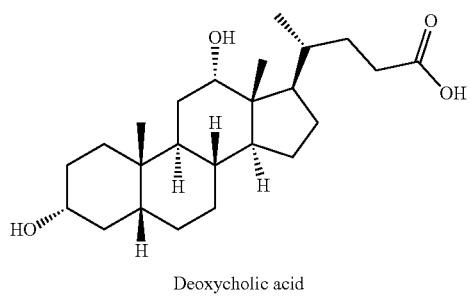
Deoxycholic acid
Chemical Formula 10
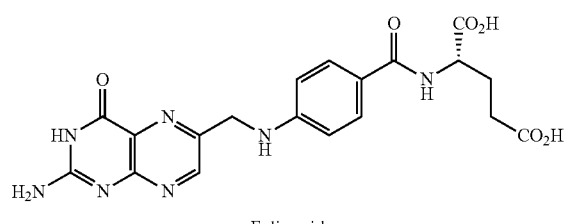
Folic acid
Chemical Formula 11
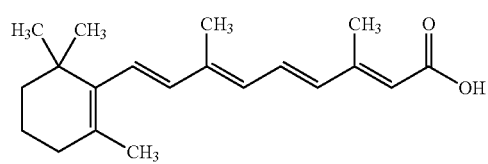
Retinoic acid
Chemical Formula 12
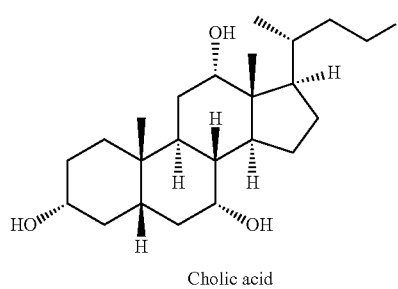
Cholic acid
Chemical Formula 13
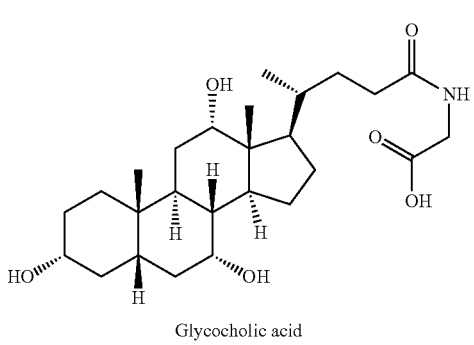
Glycocholic acid
Chemical Formula 14
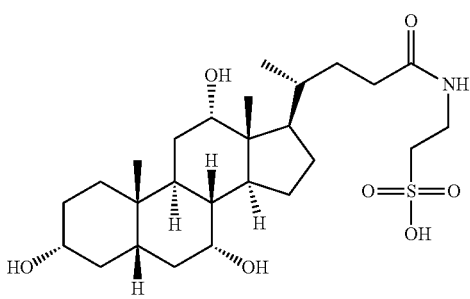
Taurocholic acid
Chemical Formula 15
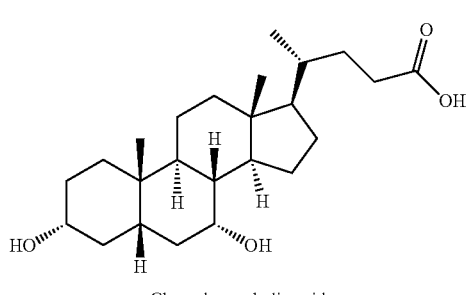
Chenodeoxycholic acid
Chemical Formula 16
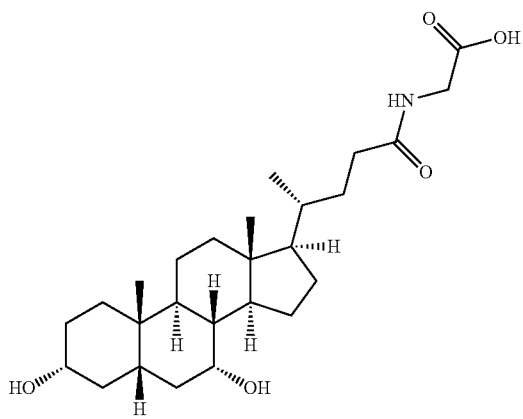
Glycochenodeoxycholic acid
Chemical Formula 17
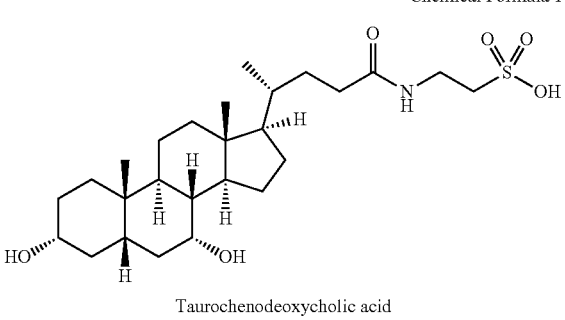
Taurochenodeoxycholic acid

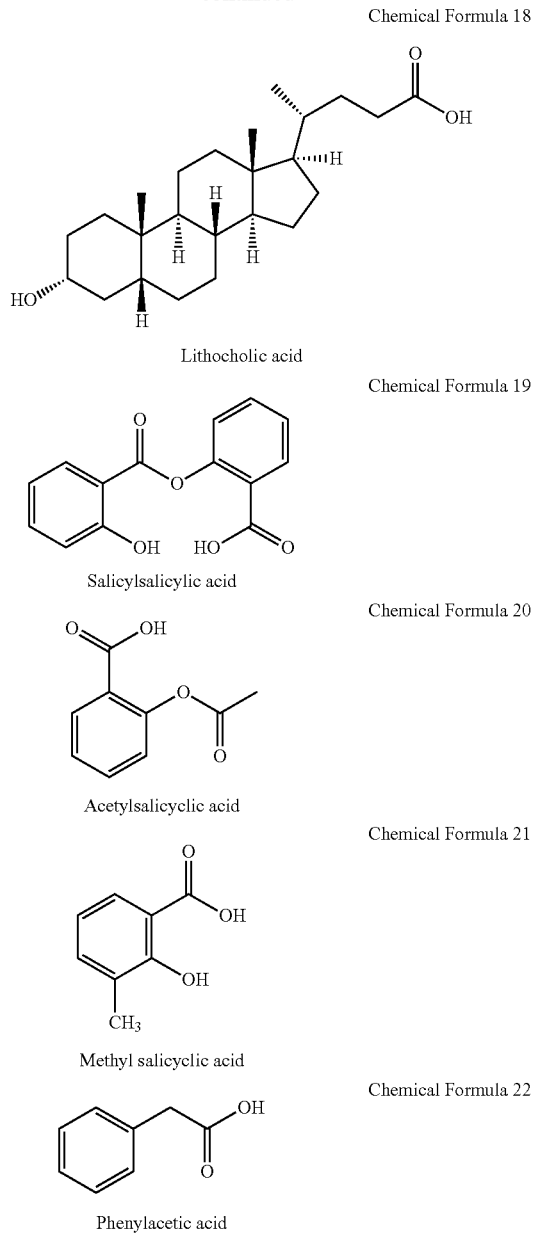

Chemical Formula 18

Lithocholic acid

Chemical Formula 19

Salicylsalicylic acid

Chemical Formula 20

Acetylsalicyclic acid

Chemical Formula 21

Methyl salicyclic acid

Chemical Formula 22

Phenylacetic acid

The methylene blue has a bactericidal effect on specific bacteria as the antimicrobial effect. In addition, the methylene blue is a dye to which a phenothiazine group is bound and reacts with the phenothiazine group when light is irradiated to transfer energy to the surrounding oxygen, and active oxygen (singlet oxygen) is generated to affect surrounding bacteria, thereby exhibiting a sterilization effect.

The methylene blue is a positively charged dye and the methylene blue itself is very difficult to be introduced into the skin and the cells, but the methylene blue mixture in accordance with exemplary embodiments of the present invention contains methylene blue having a positively charged characteristic and one or more kinds of organic acids of fatty acids having negatively charged and hydrophobic characteristics to neutralize the charge, has hydrophobicity due to a structural characteristic to have relatively high permeability to the skin composed of mixed lipids, and has easiness even in penetration into the pores and the like.

In one exemplary embodiment, the methylene blue mixture may be prepared by a method of mixing methylene blue with an organic acid to form a methylene blue-organic acid mixture, lyophilizing the mixture to form a complex, and mixing the resulting complex with another organic acid, but the present invention is not necessarily limited thereto.

Exemplary embodiments of the present invention relate to a wound dressing for promoting wound healing by preventing infections of the wound surface in which continuity of the body tissue is damaged by a physical impact and the like and an attached surface of the wound dressing, in which the wound dressing uses a transdermal material prepared by a hydrocolloid gel, a polyurethane film, a PVA hydrogel, an alginate gel or the like and an active ingredient for helping in skin wound protection and wound healing used in the wound dressing uses a mixture of a methylene blue component used as a photosensitizer for photodynamic therapy in various skin diseases and an organic acid for imparting a property change and material stability to the methylene blue component. Therefore, it is possible to help in preventing infection and healing wounds as compared with a conventional wound dressing, affect bacteria on the attached surface of the wound dressing or the lesion, and particularly have an effect of preventing the infection from external harmful bacteria relatively more than the related art in an environment where light is irradiated.

Hereinafter, Embodiments of the present invention will be described in more detail with reference to Examples. These Examples are only for describing the present invention in more detail, and it will be apparent to those skilled in the art that the scope of the present invention is not limited by these Examples.

EXAMPLES

Example 1

Hydrophobicization of Methylene Blue and Organic Acid (1) Hydrophobicization of Methylene Blue/DHA by Electrostatic Force 20 mg of methylene blue (MB, purchased from Aldrich) and 20 mg of DHA (D, purchased from Aldrich) were heated in 50 mL of tetrahydrofuran (THF, purchased from Daejeon Chemical) at 60 to 90° C. for 1 to 5 minutes and the methylene blue was dissolved. The mixture in which methylene blue was dissolved was filtered using a hydrophobic injection filter (0.2 μm), and the obtained filtrate was dried. The hydrophobized methylene blue dissolved in the organic layer was extracted using chloroform and water, purified and lyophilized to obtain MBD (methylene blue hydrophobized with DHA).

(2) Hydrophobicization of Methylene Blue/IAA by Electrostatic Force 20 mg of methylene blue (MB, purchased from Aldrich) and 20 mg of IAA (I, purchased from Aldrich) were heated in 50 mL of tetrahydrofuran (THF, purchased from Daejeon Chemical) at 60 to 90° C. for 1 to 5 minutes and the methylene blue was dissolved. The mixture in which methylene blue was dissolved was filtered using a hydrophobic injection filter (0.2 μm), and the obtained filtrate was dried. The hydrophobized methylene blue dissolved in the organic layer was extracted using chloroform and water, purified and lyophilized to obtain MBI (methylene blue hydrophobized with IAA).

(3) Hydrophobicization of Methylene Blue/Tranexamic Acid by Electrostatic Force 20 mg of methylene blue (MB, purchased from Aldrich) and 20 mg of tranexamic acid (T, purchased from Aldrich) were heated in 50 mL of tetrahydrofuran (THF, purchased from Daejeon Chemical) at 60 to 90° C. for 1 to 5 minutes and the methylene blue was dissolved. The mixture in which methylene blue was dissolved was filtered using a hydrophobic injection filter (0.2 μm), and the obtained filtrate was dried. The hydrophobized methylene blue dissolved in the organic layer was extracted using chloroform and water, purified and lyophilized to obtain MBT (methylene blue hydrophobized with tranexamic acid).

(4) Hydrophobicization of Methylene Blue/Salicylate by Electrostatic Force 20 mg of methylene blue (MB, purchased from Aldrich) and 20 mg of salicylate (S, purchased from Aldrich) were heated in 50 mL of tetrahydrofuran (THF, purchased from Daejeon Chemical) at 60 to 90° C. for 1 to 5 minutes and the methylene blue was dissolved. The mixture in which methylene blue was dissolved was filtered using a hydrophobic injection filter (0.2 μm), and the obtained filtrate was dried. The hydrophobized methylene blue dissolved in the organic layer was extracted using chloroform and water, purified and lyophilized to obtain MBS (methylene blue hydrophobized with salicylate).

(5) Hydrophobicization of Methylene Blue/Ascorbic Acid by Electrostatic Force 20 mg of methylene blue (MB, purchased from Aldrich) and 20 mg of ascorbic acid(A, purchased from Aldrich) were heated in 50 mL of tetrahydrofuran (THF, purchased from Daejeon Chemical) at 60 to 90° C. for 1 to 5 minutes and the methylene blue was dissolved. The mixture in which methylene blue was dissolved was filtered using a hydrophobic injection filter (0.2 μm), and the obtained filtrate was dried. The hydrophobized methylene blue dissolved in the organic layer was extracted using chloroform and water, purified and lyophilized to obtain MBA (methylene blue hydrophobized with ascorbic acid).

Example 2

Formation of Mixture Using Hydrophobized Methylene Blue and Another Organic Acid or Surfactant with Organic Acid Preparation and evaluation of mixture containing hydrophobized methylene blues MBD, MBI, MBT, MBS, and MBA and amphiphilic material by each organic acid A mixture MBDs was prepared using 0.2 mg of MBD obtained in Example 2 (1) above and 2 mL of an aqueous solution in which 20 mg of an oleate (purchased from Aldrich) was dissolved.

Further, 0.2 mg of each of MBI, MBT, MBS and MBA obtained in Example 2 (2) to (5) above was sufficiently dispersed using 2 mL of an aqueous solution in which 20 mg of an oleate was dissolved to prepare mixtures MBIs, MBTs, MBSs and MBAs of each hydrophobized photosensitizer and oleic acid.

Figure 3:
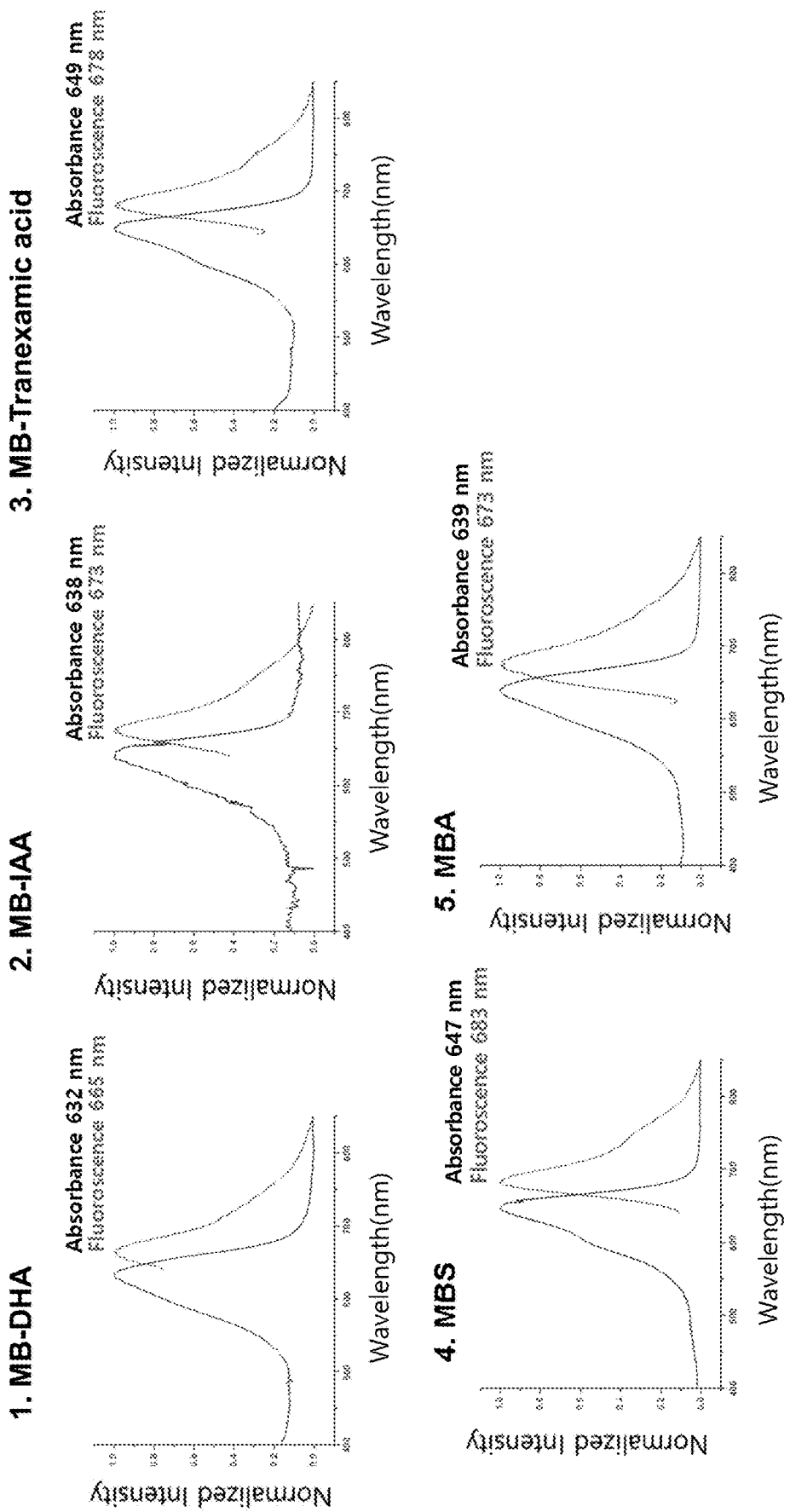
FIG. 3 is a graph illustrating absorbance and fluorescence of mixtures MBDs, MBIs, MBTs, MBSs, and MBAs using hydrophobized methylene blue and another organic acid or a surfactant together with the organic acid as the active ingredient for the prevention of infection or promotion of wound healing, which protect skin wounds and kill surrounding harmful bacteria in accordance with one exemplary embodiment of the present invention.

As results of measuring absorbance and fluorescence of mixtures MBDs, MBIs, MBTs, MBSs and MBAs formed by a methylene blue solution (MB Sol.) dissolved in water, each component of the hydrophobized methylene blue dispersed in the water, and oleic acid, it was confirmed that an absorption wavelength and a fluorescence wavelength of the methylene blue dissolved in the water were shifted to a short wavelength region by forming the mixtures and it was illustrated in FIG. 3.

In a process through Example 1 above, the methylene blue was hydrophobized with organic acid for electrostatic neutralization of methylene blue, and from Example 2 using this, it was confirmed that an efficient mixture of oleic acid as a fatty acid and hydrophobized methylene blue can be formed in an aqueous environment.

Example 3

Evaluation of Photo-Toxicity and Dark-Toxicity Against *Staphylococcus aureus* of Mixtures MBDs, MBIs, MBTs, MBSs, and MBAs Using Hydrophobized Methylene Blue and Another Organic Acid or Surfactant with Organic Acid (1) Evaluation of Photo-Toxicity Using *Staphylococcus aureus*

① Evaluation of Photo-Toxicity of MBDs

To evaluate the photo-toxicity on the bacteria according to the concentration of the mixtures MBDs prepared in Example 1 and Example 2, 1 mL of a culture solution (LB medium), in which $1 \times 10^6$/mL of *S. aureus* was dispersed, was added to each well of a 12-well plate and added with 0.5 mL of the mixtures for each concentration (final concentrations: 40.4 mg/mL, 20.2 mg/mL, 8.08 mg/mL, 4.04 mg/mL, 0 mg/mL). After 10 minutes, light was irradiated for 10 minutes (Intensity 4) using Healite II 633 (purchased from Lutronics Inc.) for photo-toxicity evaluation. The bacteria for each concentration after irradiation was diluted to $1 \times 10^{-6}$, and 1 mL of the bacteria was inoculated into a petrifilm (purchased from 3M) and incubated for 24 hours in an incubator (37° C.), and then the number of bacteria was measured.

As a control experiment, an MB aqueous solution corresponding to each concentration of the mixture was prepared, and the number of bacteria was measured by the same procedure as described above.

② Evaluation of Photo-Toxicity of MBIs

To evaluate the photo-toxicity on the bacteria according to the concentration of the mixtures MBIs prepared in Example 1 and Example 2, 1 mL of a culture solution (LB medium), in which $1 \times 10^6$/mL of *S. aureus* was dispersed, was added to each well of a 12-well plate and added with 0.5 mL of the mixtures for each concentration (final concentrations: 40.4 mg/mL, 20.2 mg/mL, 8.08 mg/mL, 4.04 mg/mL, 0 mg/mL). After 10 minutes, light was irradiated for 10 minutes (Intensity 4) using Healite II 633 (purchased from Lutronics Inc.) for photo-toxicity evaluation. The bacteria for each concentration after irradiation was diluted to $1 \times 10^{-6}$, and 1 mL of the bacteria was inoculated into a petrifilm (purchased from 3M) and incubated for 24 hours in an incubator (37° C.), and then the number of bacteria was measured.

As a control experiment, an MB aqueous solution corresponding to each concentration of the mixture was prepared, and the number of bacteria was measured by the same procedure as described above.

③ Evaluation of Photo-Toxicity of MBTs

To evaluate the photo-toxicity on the bacteria according to the concentration of the mixtures MBTs prepared in Example 1 and Example 2, 1 mL of a culture solution (LB medium), in which $1 \times 10^6$/mL of *S. aureus* was dispersed, was added to each well of a 12-well plate and added with 0.5 mL of the mixtures for each concentration (final concentrations: 40.4 mg/mL, 20.2 mg/mL, 8.08 mg/mL, 4.04 mg/mL, 0 mg/mL). After 10 minutes, light was irradiated for 10 minutes (Intensity 4) using Healite II 633 (purchased from Lutronics Inc.) for photo-toxicity evaluation. The bacteria for each concentration after irradiation was diluted to $1\times10^{-6}$, and 1 mL of the bacteria was inoculated into a petrifilm (purchased from 3M) and incubated for 24 hours in an incubator (37° C.), and then the number of bacteria was measured.

As a control experiment, an MB aqueous solution corresponding to each concentration of the mixture was prepared, and the number of bacteria was measured by the same procedure as described above.

④ Evaluation of Photo-Toxicity of MBSs

To evaluate the photo-toxicity on the bacteria according to the concentration of the mixtures MBSs prepared in Example 1 and Example 2, 1 mL of a culture solution (LB medium), in which $1\times10^6$/mL of *S. aureus* was dispersed, was added to each well of a 12-well plate and added with 0.5 mL of the mixtures for each concentration (final concentrations: 40.4 mg/mL, 20.2 mg/mL, 8.08 mg/mL, 4.04 mg/mL, 0 mg/mL). After 10 minutes, light was irradiated for 10 minutes (Intensity 4) using Healite II 633 (purchased from Lutronics Inc.) for photo-toxicity evaluation. The bacteria for each concentration after irradiation was diluted to $1\times10^{-6}$, and 1 mL of the bacteria was inoculated into a petrifilm (purchased from 3M) and incubated for 24 hours in an incubator (37° C.), and then the number of bacteria was measured.

As a control experiment, an MB aqueous solution corresponding to each concentration of the mixture was prepared, and the number of bacteria was measured by the same procedure as described above.

⑤ Evaluation of Photo-Toxicity of MBAs

To evaluate the photo-toxicity on the bacteria according to the concentration of the mixtures MBAs prepared in Example 1 and Example 2, 1 mL of a culture solution (LB medium), in which $1\times10^6$/mL of *S. aureus* was dispersed, was added to each well of a 12-well plate and added with 0.5 mL of the mixtures for each concentration (final concentrations: 40.4 mg/mL, 20.2 mg/mL, 8.08 mg/mL, 4.04 mg/mL, 0 mg/mL). After 10 minutes, light was irradiated for 10 minutes (Intensity 4) using Healite II 633 (purchased from Lutronics Inc.) for photo-toxicity evaluation. The bacteria for each concentration after irradiation was diluted to $1\times10^{-6}$, and 1 mL of the bacteria was inoculated into a petrifilm (purchased from 3M) and incubated for 24 hours in an incubator (37° C.), and then the number of bacteria was measured.

As a control experiment, an MB aqueous solution corresponding to each concentration of the mixture was prepared, and the number of bacteria was measured by the same procedure as described above.

(2) Evaluation of Dark-Toxicity Using *Staphylococcus aureus*

① Evaluation of Dark-Toxicity of MBDs

To evaluate the dark-toxicity on the bacteria according to the concentration of the mixtures MBDs prepared in Example 1 and Example 2, 1 mL of a culture solution (LB medium), in which $1\times10^6$/mL of *S. aureus* was dispersed, was added to each well of a 12-well plate and added with 0.5 mL of the mixtures for each concentration (final concentrations: 40.4 mg/mL, 20.2 mg/mL, 8.08 mg/mL, 4.04 mg/mL, 0 mg/mL). The bacteria for each concentration was diluted to $1\times10^{-6}$, and 1 mL of the bacteria was inoculated into a petrifilm (purchased from 3M) and incubated for 24 hours in an incubator (37° C.), and then the number of bacteria was measured. As a control experiment, an MB aqueous solution corresponding to each concentration of the mixture was prepared, and the number of bacteria was measured by the same procedure as Example 3 (1) ① above. All the procedures were performed in a dark room where light was blocked.

② Evaluation of Dark-Toxicity of MBIs

To evaluate the dark-toxicity on the bacteria according to the concentration of the mixtures MBIs prepared in Example 1 and Example 2, 1 mL of a culture solution (LB medium), in which $1\times10^6$/mL of *S. aureus* was dispersed, was added to each well of a 12-well plate and added with 0.5 mL of the mixtures for each concentration (final concentrations: 40.4 mg/mL, 20.2 mg/mL, 8.08 mg/mL, 4.04 mg/mL, 0 mg/mL). The bacteria for each concentration was diluted to $1\times10^{-6}$, and 1 mL of the bacteria was inoculated into a petrifilm (purchased from 3M) and incubated for 24 hours in an incubator (37° C.), and then the number of bacteria was measured. As a control experiment, an MB aqueous solution corresponding to each concentration of the mixture was prepared, and the number of bacteria was measured by the same procedure as Example 3 (1) ② above. All the procedures were performed in a dark room where light was blocked.

③ Evaluation of Dark-Toxicity of MBTs

To evaluate the dark-toxicity on the bacteria according to the concentration of the mixtures MBTs prepared in Example 1 and Example 2, 1 mL of a culture solution (LB medium), in which $1\times10^6$/mL of *S. aureus* was dispersed, was added to each well of a 12-well plate and added with 0.5 mL of the mixtures for each concentration (final concentrations: 40.4 mg/mL, 20.2 mg/mL, 8.08 mg/mL, 4.04 mg/mL, 0 mg/mL). The bacteria for each concentration was diluted to $1\times10^{-6}$, and 1 mL of the bacteria was inoculated into a petrifilm (purchased from 3M) and incubated for 24 hours in an incubator (37° C.), and then the number of bacteria was measured. As a control experiment, an MB aqueous solution corresponding to each concentration of the mixture was prepared, and the number of bacteria was measured by the same procedure as Example 3 (1) ③ above. All the procedures were performed in a dark room where light was blocked.

④ Evaluation of Dark-Toxicity of MBSs

To evaluate the dark-toxicity on the bacteria according to the concentration of the mixtures MBSs prepared in Example 1 and Example 2, 1 mL of a culture solution (LB medium), in which $1\times10^6$/mL of *S. aureus* was dispersed, was added to each well of a 12-well plate and added with 0.5 mL of the mixtures for each concentration (final concentrations: 40.4 mg/mL, 20.2 mg/mL, 8.08 mg/mL, 4.04 mg/mL, 0 mg/mL). The bacteria for each concentration was diluted to $1\times10^{-6}$, and 1 mL of the bacteria was inoculated into a petrifilm (purchased from 3M) and incubated for 24 hours in an incubator (37° C.), and then the number of bacteria was measured. As a control experiment, an MB aqueous solution corresponding to each concentration of the mixture was prepared, and the number of bacteria was measured by the same procedure as Example 3 (1) ④ above. All the procedures were performed in a dark room where light was blocked.

⑤ Evaluation of Dark-Toxicity of MBAs

To evaluate the dark-toxicity on the bacteria according to the concentration of the mixtures MBAs prepared in Example 1 and Example 2, 1 mL of a culture solution (LB medium), in which $1\times10^6$/mL of *S. aureus* was dispersed, was added to each well of a 12-well plate and added with 0.5 mL of the mixtures for each concentration (final concentrations: 40.4 mg/mL, 20.2 mg/mL, 8.08 mg/mL, 4.04 mg/mL, 0 mg/mL). The bacteria for each concentration was diluted to $1\times10^{-6}$, and 1 mL of the bacteria was inoculated into a petrifilm (purchased from 3M) and incubated for 24 hours in an incubator (37° C.), and then the number of bacteria was measured. As a control experiment, an MB aqueous solution corresponding to each concentration of the mixture was prepared, and the number of bacteria was measured by the same procedure as Example 3 (1) ⑤ above. All the procedures were performed in a dark room where light was blocked.

Figure 4:
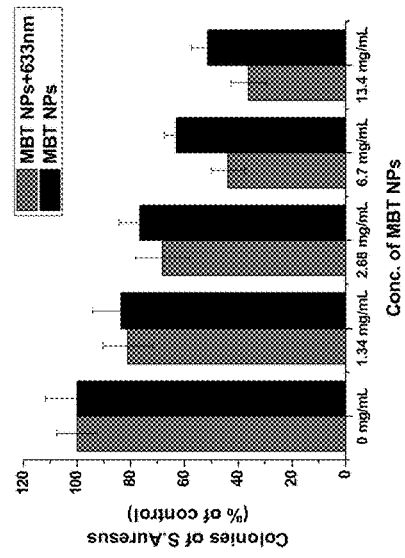
FIG. 4 illustrates results for a sterilization effect according to light irradiation to *Staphylococcus aureus* of mixtures MBDs, MBIs, MBTs, MBSs, and MBAs using hydrophobized methylene blue and another organic acid or a surfactant together with the organic acid as the active ingredient for the prevention of infection or promotion of wound healing, which protect skin wounds and kill surrounding harmful bacteria in accordance with one exemplary embodiment of the present invention.
Figure 4:
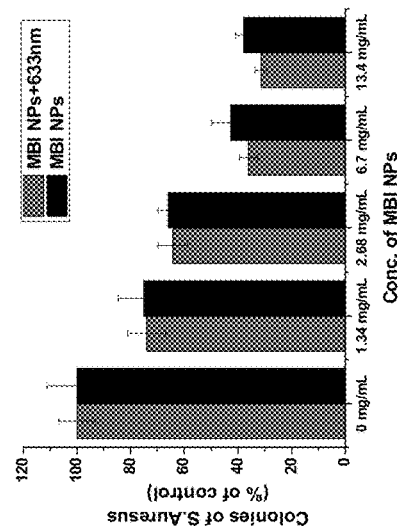
Figure 4:
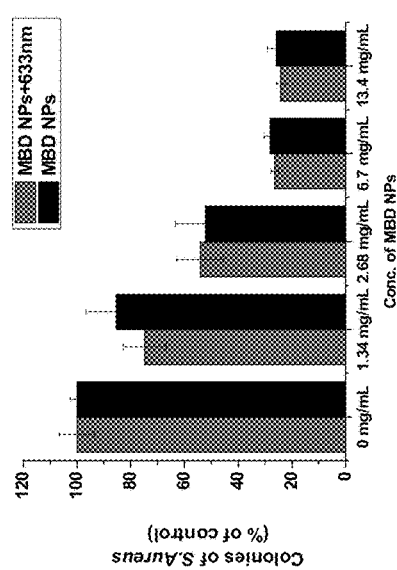
Figure 4:
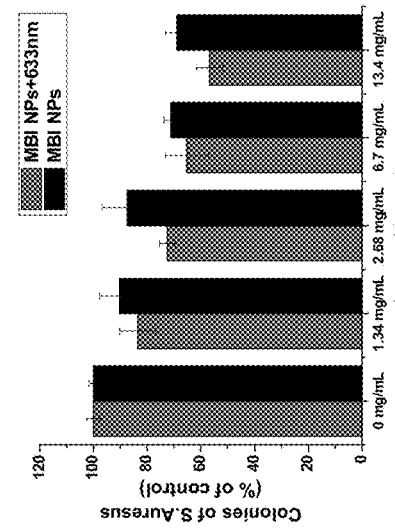
Figure 4:
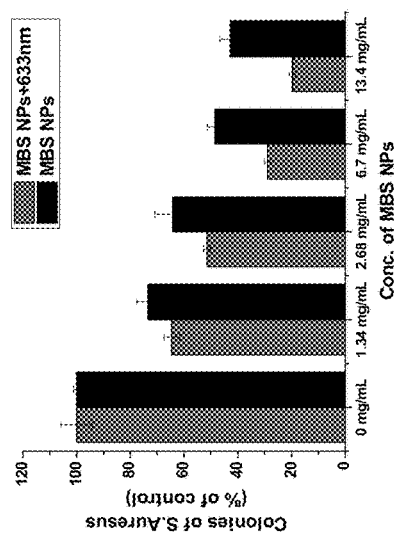

The evaluation of (1) photo-toxicity and (2) dark-toxicity of Example 3 was illustrated in FIG. 4.

Example 4

Preparation of Patch-Type Wound Dressing Using Hydrocolloid Gel and Preparation of Wound Dressing Containing Methylene Blue Mixture A quadrangular patch-type transdermal material having a width of 10 cm and a length of 10 cm was prepared by using a hydrocolloid gel and a methylene blue mixture formed by mixing methylene blue, salicylic acid and oleic acid was uniformly applied to the transdermal material by 30 μg per a unit area of a width of 1 cm and a length of 1 cm. Thereafter, the hydrocolloid gel which was uniformly applied with the mixture was dried to prepare a wound dressing containing the methylene blue mixture.

Example 5

Evaluation of Photo-Toxicity and Dark-Toxicity Against *Staphylococcus aureus* of Wound Dressing Containing Mixture Using Hydrophobized Methylene Blue and Another Organic Acid or Surfactant with Organic Acid (1) Evaluation of Photo-Toxicity Using *Staphylococcus aureus*

To evaluate the photo-toxicity on bacteria of the wound dressing containing the methylene blue mixture prepared in Example 4, an agar medium inoculated with *S. aureus* was prepared, the wound dressing containing the blue mixture was added to each well of a 12-well plate, and the application surface of the methylene blue mixture was brought into contact with the agar medium. After 10 minutes, light was irradiated for 10 minutes (Intensity 4) using Healite II 633 (purchased from Lutronics Inc.) for photo-toxicity evaluation. After the light irradiation, each wound dressing was removed and the bacteria were cultured in an incubator (37° C.) for 24 hours and then the number of bacteria was measured.

As a control experiment, after the inoculation, an untreated group and a wound dressing without applying the methylene blue mixture were prepared, and the number of the bacteria was measured by the same procedure as above procedure.

(2) Evaluation of Dark-Toxicity Using *Staphylococcus aureus*

To evaluate the dark-toxicity on bacteria of the wound dressing containing the methylene blue mixture prepared in Example 4, an agar medium inoculated with *S. aureus* was prepared, the wound dressing containing the blue mixture was added to each well of a 12-well plate, and the application surface of the methylene blue mixture was brought into contact with the agar medium. After 10 minutes, to evaluate the dark-toxicity, each wound dressing was removed and the bacteria were cultured in an incubator (37° C.) for 24 hours and then the number of bacteria was measured.

As a control experiment, after the inoculation, an untreated group and a wound dressing without applying the methylene blue mixture were prepared, and the number of the bacteria was measured by the same procedure as Example 5 (1) above. All the procedures were performed in a dark room where light was blocked.

Figure 5:
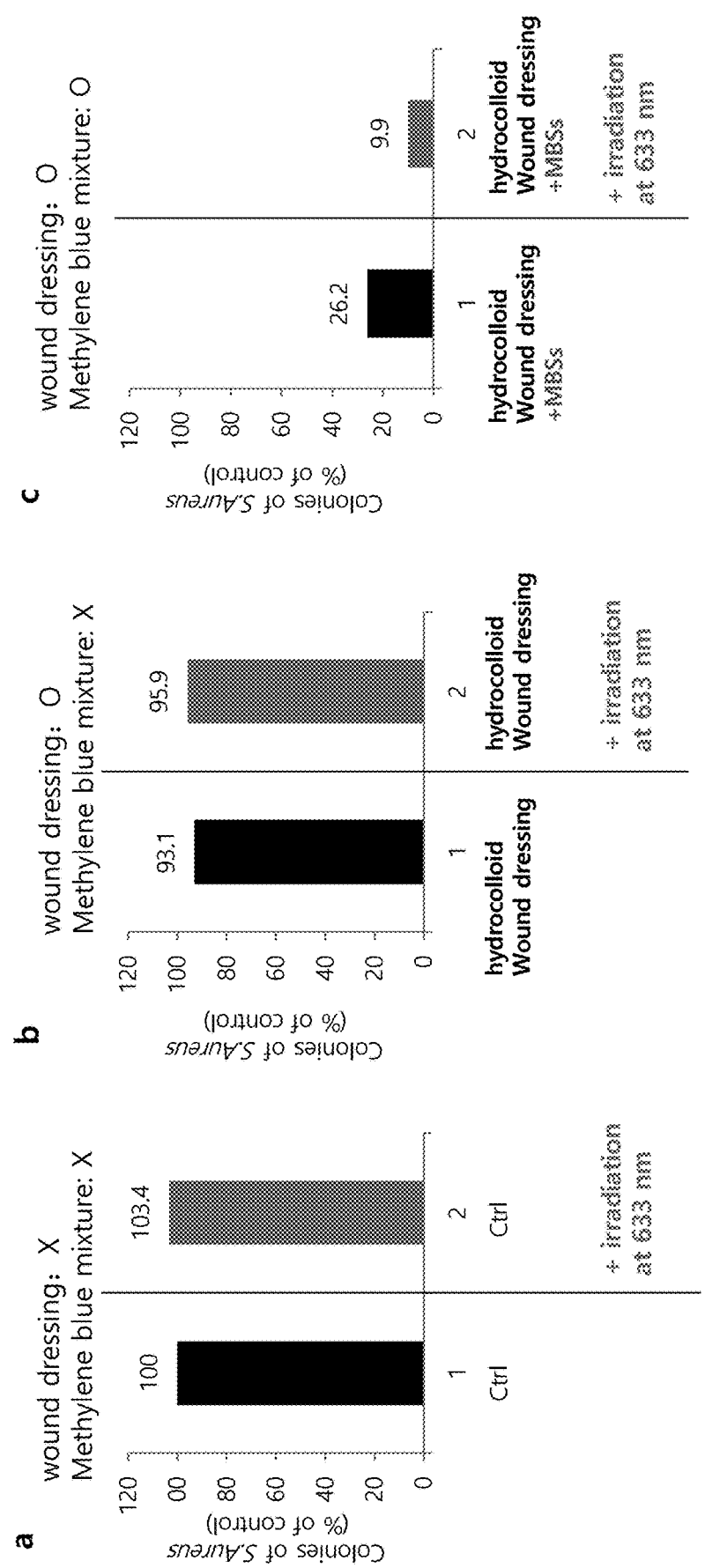
FIG. 5 illustrates results for a sterilization effect according to light irradiation in the case of using a wound dressing containing a mixture composed of methylene blue-organic acid-oleic acid, which is an active ingredient for the prevention of infection or promotion of wound healing, which protect skin wounds and kill surrounding harmful bacteria in accordance with one exemplary embodiment of the present invention.

The evaluation of (1) photo-toxicity and (2) dark-toxicity of Example 5 was illustrated in FIG. 5.

As a result of the experiment, in the untreated group after the inoculation, the number of *Staphylococcus aureus* was almost not reduced irrespective of the presence or absence of light irradiation (FIG. 5A), and when a wound dressing without applying the methylene blue mixture of the present invention was used, the number of *Staphylococcus aureus* was reduced to a negligible level irrespective of the presence or absence of light irradiation (FIG. 5B). On the other hand, when the wound dressing applied with the methylene blue mixture prepared in the present invention was used, the number of *Staphylococcus aureus* was remarkably reduced (FIG. 5C). From the above results, it was proved that the wound dressing applied with the methylene blue mixture of the present invention was excellent in bactericidal action irrespective of the presence or absence of light irradiation, and particularly, much excellent in bactericidal action when light was irradiated.

What is claimed is:

1. A wound dressing for protection and prevention of infection of a damaged region of skin, comprising a transdermal material for attaching the wound dressing to the skin and a composition for wound healing including a mixture of methylene blue and two kinds of organic acids applied to the transdermal material,
    wherein the two kinds of organic acids are selected from docosahexaenoic acid (DHA), indole-3-acetic acid (IAA), tranexamic acid, salicylic acid, ascorbic acid, linoleic acid, linolenic acid, oleic acid, salicylsalicylic acid, acetylsalicylic acid, methyl salicylic acid, and phenylacetic acid,
    wherein a first kind of the two kinds of organic acids are selected from DHA, IAA, tranexamic acid, salicylic acid, ascorbic acid, salicylsalicvlic acid, acetylsalicylic acid, methyl salicylic acid, and phenylacetic acid, and a second kind of the two kinds of organic acids are selected from linoleic acid, linolenic acid, and oleic acid, and
    wherein the methylene blue and two kinds of organic acids form a complex structure where the methylene blue and the first kind of organic acids are positioned in a center without the second kind of organic acids, and the second kind of organic acids are positioned without the first kind of organic acids around the methylene blue and the first kind of organic acids.

2. The wound dressing of claim 1, wherein the transdermal material is made of at least one selected from a hydrocolloid gel, a polyurethane film, a PVA hydrogel, an alginate gel, and a mixture thereof.

3. The wound dressing of claim 1, wherein the mixture of the methylene blue and the two kinds of organic acids applied on the wound dressing is contained with 0.1 to 100 μg per a unit area of 1 cm of a width and 1 cm of a length of the transdermal material.

4. The wound dressing of claim 1, wherein the mixture of the methylene blue and the two kinds of organic acids applied on the wound dressing is contained with 10 to 50 µg per a unit area of 1 cm of a width and 1 cm of a length of the transdermal material.

5. The wound dressing of claim 1, wherein in a mass ratio of the methylene blue and two kinds of organic acids, the mass of the first organic acid is 1 to 5 times greater than the mass of the methylene blue, and the mass of the second organic acid is 50 to 500 times greater than the mass of the mixture of the methylene blue and the first organic acid.

6. The wound dressing of claim 1, wherein the methylene blue is positively charged, and the two kinds of organic acids are negatively charged and hydrophobic.

\* \* \* \* \*